United States Patent [19]

Kempe et al.

[11] Patent Number: 4,866,183

[45] Date of Patent: Sep. 12, 1989

[54] PREPARATION OF HEXAARYLBISIMIDAZOLES

[75] Inventors: Uwe Kempe, Dannstadt-Schauernheim; Toni Dockner, Meckenheim; Helmut Karn, Ludwigshafen; Thomas Bluemel, Erpolzheim; Reinhold J. Leyrer, Ludwigshafen; Thomas Loerzer, Frankenthal, all of Fed. Rep. of Germany

[73] Assignee: BASF Aktiengesellschaft, Ludwigshafen, Fed. Rep. of Germany

[21] Appl. No.: 59,796

[22] Filed: Jun. 9, 1987

[30] Foreign Application Priority Data

Jun. 18, 1986 [DE] Fed. Rep. of Germany ....... 3620430

[51] Int. Cl.$^4$ ............................................. C07D 233/88
[52] U.S. Cl. .................................. 548/336; 548/346
[58] Field of Search ......................................... 548/336

[56] References Cited

PUBLICATIONS

Maeda, K., et al., *Bull. Chem. Soc. Jap.* 43 (1970), 429–438.
Cescon, L., et al., *J. Org. Chem.* 36 (1971), 2262–2267.
Dehmlow, E., et al., *Phase Transfer Catalysis*, Verlag Chemie, Weinheim, 1980, pp. 1—3.

*Primary Examiner*—Richard A. Schwartz
*Attorney, Agent, or Firm*—John H. Shurtleff

[57] ABSTRACT

Hexaarylbisimidazoles I

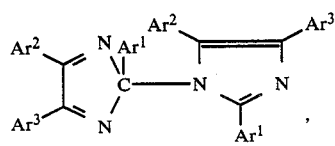

where $Ar^1$, $Ar^2$ and $Ar^3$ are each aryl, of which $Ar^2$ and $Ar^3$ can be linked to form an anellated ring system, are prepared by oxidizing the corresponding triarylimidazoles II

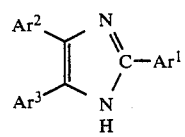

in an aqueous/organic two-phase system in the presence of active amounts of an onium salt III.

8 Claims, No Drawings

PREPARATION OF HEXAARYLBISIMIDAZOLES

The present invention relates an improved process for preparing a hexaarylbisimidazole of the formula I

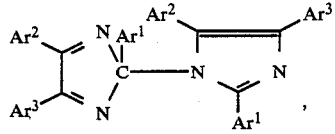

where $Ar^1$, $Ar^2$ and $Ar^3$ are each aryl, of which $Ar^2$ and $Ar^3$ can also be linked to each other to form a fused ring system, by oxidizing the corresponding triarylimidazole II

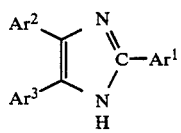

in an aqueous/organic two-phase system.

It is generally known, for example from Bull. Chem. Soc. Jap. 43 (1970), 429-38, that hexaarylbisimidazoles can be synthesized by oxidation of corresponding triarylimidazoles. The oxidation is effected either in a homogeneous solvent (for example benzene) or a solvent mixture (for example water/ethanol) or in an aqueous/organic two-phase system where benzene is used as the organic phase. The two-phase reaction is more advantageous, according to J. Org. Chem. 36 (1971), 2262-7, because of its greater versatility and for preparing relatively large amounts. However, the disadvantage with this process is the long reaction time of 16 hours.

The oxidants used in the heterogeneous system are aqueous, alkaline potassium hexacyanoferrate-(III) solutions. Oxidants in the homogeneous phase are in addition hypohalites or lead dioxide.

It is an object of the present invention to provide an effective process for preparing a hexaarylbisimidazole, which permits carrying out the reaction on an industrial scale in a high yield in as short a reaction time as possible.

We have found that this object is achieved with a process for preparing a hexaarylbisimidazole of the formula I

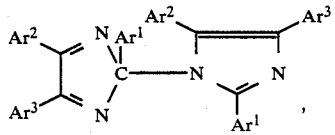

where $Ar^1$, $Ar^2$ and $Ar^3$ are each aryl, of which $Ar^2$ and $Ar^3$ can also be linked to each other to form a fused ring system, by oxidizing the corresponding triarylimidazole II

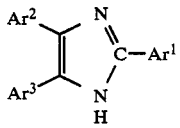

in an aqueous/organic two-phase system, which comprises carrying out the oxidation in the presence of an active amount of an onium salt III.

A suitable onium salt III is in principle any compound of this type, including in particular quaternary ammonium, phosphonium, arsonium and ternary sulfonium salt. The preferred onium salts can be represented by the general formulae IIIa and IIIb $$R_4M^{\oplus}X^{\ominus} \quad \text{IIIa}$$

$$R_3S^{\oplus}X^{\ominus} \quad \text{IIIb,}$$

where R is identical or different hydrocarbyl, for example alkyl, cycloalkyl, aryl or aralkyl, M is phosphorus, arsenic or nitrogen and $X^{\ominus}$ is the anion equivalent of a mineral acid.

In general the hydrocarbyls in the compounds IIIa and IIIb are branched or preferably unbranched $C_1$-$C_{20}$-alkyl, $C_5$- or $C_6$-cycloalkyl, aryl or aralkyl of 6 or 7 to 20 carbon atoms, for example phenyl, p-tolyl or benzyl. Two of the alkyls R can also be bonded to each other, for example to form a 5- or 6-membered ring, for example a piperidine ring. Preferably the total number of carbon atoms in the radicals R is not greater than 25.

Suitable anions $X^{\ominus}$ are in particular the anions of organic, or preferably inorganic, monobasic acids. Examples are $F^{\ominus}$, $Cl^{\ominus}$, $Br^{\ominus}$, $I^{\ominus}$, $NO_3^{\ominus}$, $HSO_4^{\ominus}$, $HCO_3^{\ominus}$, $CH_3CO_2^{\ominus}$ or $C_6H_5CO_2^{\ominus}$. A list of further anions can be found in E. V. Dehmlow and S. S. Dehmlow, Phase Transfer Catalysis, 2nd edition, (1983), 14-16.

Owing to the general suitability of the onium salts, which one is chosen depends chiefly on availability and price. In practice, the choice will therefore be in particular an ammonium salt, especially an ammonium bromide or chloride, chiefly the commercially available and easily prepared tetrabutylammonium bromide. Other prime candidates are those ammonium salts where three of the radicals R are lower alkyl, such as methyl, ethyl, propyl or butyl, and the fourth is benzyl or unbranched $C_6$-$C_{19}$-alkyl.

The most readily available phosphonium and arsonium salts are those which are derived from triphenylphosphine and triphenylarsine and whose fourth substituent is introduced into the molecule by quaternization, for example with a $C_1$-$C_7$-alkyl bromide. Also suitable are tetraphenylphosphonium and tetraphenylarsonium halides.

Suitable sulfonium salts are for example triphenylsulfonium salts or the easily prepared trimethylsulfonium iodide. In general, phosphonium and ammonium salts are preferable to sulfonium and arsonium salts.

The amount of onium salt is not especially critical. To obtain effective acceleration, even catalytic amounts, for example from 0.5 to 20, in particular from 1 to 15, mol%, based on starting material II, are sufficient. It is of course also possible to use larger, for example stoichiometric, amounts, but in general this brings no further benefits.

The oxidant used can be a prior art substance. It is advantageous to use an alkaline earth metal hypohalite, in particular alkali metal hypohalite such as a hypochlorite or hypobromite, or an alkaline hexacyanoferrate(III) solution; sodium hypochlorites and hypobromites and potassium hexacyanoferrate(III) have proved particularly useful.

The amount of oxidant ranges expediently from 0.5 to 10 moles, in particular from 0.5 to 1 mole, per mole of imidazole II.

The imidazole II is oxidized in an aqueous/organic two-phase system. The ratio of organic:aqueous phase is not particularly critical, ranging in general from 10:1 to 1:1.

The organic phase used is an aprotic solvent, for example benzene, anisole, nitrobenzene, benzonitrile, pyridine or carbon tetrachloride. Of proven suitability are in particular solvents of little or no polarity such as toluene, xylene, chloroform or methylene chloride.

In starting material II

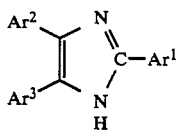
II the radicals $Ar^1$, $Ar^2$ and $Ar^3$ are each aryl, for example phenyl or naphthyl, which can carry one or more substituents inert under the reaction conditions. Suitable substituents are for example halogens, such as chlorine or bromine, $C_1$-$C_6$-alkyl or alkoxy, or nitro. The radicals $Ar^2$ and $Ar^3$ can also be linked to each other to form a fused ring system, for example a phenanthrene system.

The reaction is expediently carried out by introducing the triarylimidazole II first, in the form of a solution or suspension in the organic solvent, and adding the alkaline aqueous phase which contains the oxidant. The oxidation is advantageously carried out at from 0° to 40° C., in particular from 0° to 5° C., with thorough mixing of the two phases. It can be carried out continuously or batchwise using a technique customary for the purpose.

Using the process according to the invention, a triarylimidazole can be oxidized in a short time in a technically simple and economical manner to a hexaarylbisimidazole which is used, for example, as a photoinitiator for preparing films or dyes in transparent films.

EXAMPLES 1 TO 5

Preparation of

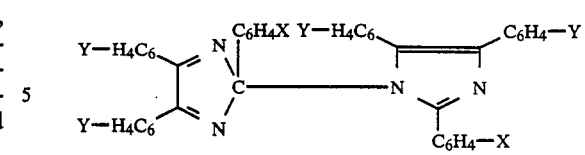

where X=Cl and Y=p-OCH$_3$ 2-(2'-Chlorophenyl)-4,5-bis(4'-methoxyphenyl)imidazole dissolved in the organic solvent was added at from 0° to 5° C. to a solution of water, ammonium halide and oxidant with thorough stirring of the resulting two-phase mixture. Stirring was continued at the stated temperature for a further period of from about 0.5 to 2.0 h (change of color from blue to yellow), and the reaction mixture was then worked up in a conventional manner by separating off the aqueous phase, washing and drying the organic phases and removing the solvent. The crude product was then treated with ethanol, whereupon it crystallized out, or recrystallized from ethanol (melting point 200°–205° C.).

Details of the reaction and yields can be found in the table below. When sodium hypochlorite is used as the oxidant, the stated amounts are based on an aqueous hypochlorite solution (a bleach liquor) with an active chlorine content of from 12.5 to 13.5%. The pH of the solution was over 12.

TABLE

| Example No. | Imidazole II g/mmol | Solvent ml | Onium salt g/mol %[a] | H$_2$O ml | NaOCl g | Oxidant K$_3$[Fe(CN)$_6$] g | KOH g | Yield g/% |
|---|---|---|---|---|---|---|---|---|
| 1 | 5.85/15.6 | toluene 100 | TBAB[b] 0.43/8 | 30 | 20 | — | — | 5.5/94 |
| 2 | 5.85/15.6 | toluene 100 | TBAB 0.4/7.7 | 190 | — | 9.9 | 8.4 | 5.8/99 |
| 3 | 5.85/15.6 | toluene 100 | BTEAC[c] 0.5/14 | 30 | 20 | — | — | 5.1/88 |
| 4 | 11.6/31 | CH$_2$Cl$_2$ 17.5 | TBAB 0.3/3.2 | — | 19 | 1 | — | 9.5/78 |
| 5 | 55/147 | CH$_2$Cl$_2$ 120 | TBAB 1.5/3.3 | — | 40.7 | — | — | 49.4/90 |

[a]based on II
[b]tetrabutylammonium bromide
[c]benzyltriethylammonium chloride

EXAMPLE 6

Preparation of

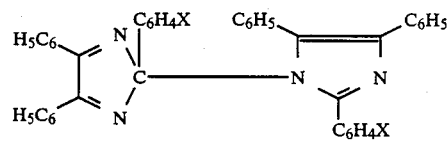

where X = Cl 50 g (0.16 mol) of 2-(2'-chlorophenyl)-4,5-diphenylimidazole were suspended in 320 ml of toluene. At from 0° to 25° C., 9.6 g (0.03 mol) of tetrabutylammonium bromide and 88 g of sodium hypochlorite solution (concentration and pH as in the preceding Examples) were added. After stirring for 5 hours, the crude product was worked up in a conventional manner and recrystallized from ether. Yield: 30.7 g of hexaarylbisimidazole (melting point 210°–212° C.)≙61.4% of theory.

We claim:

1. In a process for preparing a hexaarylbisimidazole of the formula

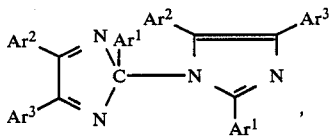

where $Ar^1$, $Ar^2$ and $Ar^3$ are each aryl, of which $Ar^2$ and $Ar^3$ can also be linked to each other to form a fused ring system, by oxidizing the corresponding triarylimidazole

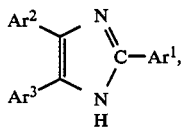

in an aqueous/organic two-phase system, the improvement which comprises:
   carrying out the oxidation in the presence of an oxidant selected from the group consisting of alkali metal hypochlorites and alkaline earth metal hypochlorites and also in the presence of an active amount of an onium salt.

2. A process as claimed in claim 1, wherein the onium salt used is a quaternary ammonium, phosphonium, arsonium or ternary sulfonium salt.

3. A process as claimed in claim 1, wherein the onium salt used is a compound of the formula IIIa or IIIb $R_4M^{\oplus}X^{\ominus}$   IIIa $R_3S^{\oplus}X^{\ominus}$   IIIb where R is alkyl, cycloalkyl, aryl or aralkyl, M is phosphorus, arsenic or nitrogen and $X^{\ominus}$ is the anion equivalent of a mineral acid.

4. A process as claimed in claim 1, wherein the onium salt is used in an amount of from 0.5 to 20 mol%, based on triarylimidazole II.

5. A process as claimed in claim 1, wherein the onium salt used is a tetraalkylammonium or trialkylbenzylammonium bromide or chloride.

6. A process as claimed in claim 1, wherein the organic phase used is an aprotic solvent of little or no polarity.

7. A process as claimed in claim 1, wherein the organic phase used is a halogenated hydrocarbon or an aromatic hydrocarbon.

8. A process as claimed in claim 1 wherein $Ar^1$, $Ar^2$ and $Ar^3$ are each selected from the group consisting of phenyl and naphthyl which can carry one or more substituents inert under the reaction conditions.

* * * * *